United States Patent [19]

Andrew et al.

[11] 4,091,021
[45] May 23, 1978

[54] AZO DYESTUFFS

[75] Inventors: Herbert Francis Andrew; David William Crichton Ramsay; Cecil Vivian Stead, all of Manchester, England

[73] Assignee: Imperial Chemical Industries Limited, London, England

[21] Appl. No.: 668,034

[22] Filed: Mar. 18, 1976

[30] Foreign Application Priority Data

Apr. 30, 1975 United Kingdom ............... 18013/75

[51] Int. Cl.² .............................................. C09B 46/00
[52] U.S. Cl. ................................ 260/191; 260/146 D; 260/146T; 260/148; 260/153; 260/154; 260/186; 260/187
[58] Field of Search ......................................... 260/191

[56] References Cited

U.S. PATENT DOCUMENTS

| 1,378,388 | 5/1921 | Susemihl .............................. 260/191 |
| 3,202,550 | 8/1965 | Grossmann et al. ........... 204/35 N X |
| 3,635,944 | 1/1972 | Litke .................................... 260/191 |
| 3,640,994 | 2/1972 | Harnish ................................ 260/191 |
| 3,755,290 | 8/1973 | Montmollin et al. ............ 260/191 X |
| 3,828,020 | 8/1974 | Tartter ................................. 260/191 |
| 3,947,435 | 3/1976 | Pechmeze et al. .............. 260/191 X |

OTHER PUBLICATIONS

Lukin et al., "Arylphosphonic Acids," in Chem. Abs. 88,177a, Vol. 68, 1968, p. 8520.

*Primary Examiner*—Allen B. Curtis
*Attorney, Agent, or Firm*—Cushman, Darby & Cushman

[57] ABSTRACT

Azo dyestuffs, which in the acid form, are represented by the formula:

$$A-N=N-M-N=N-E \qquad (1)$$

wherein
A is an aromatic radical,
M is a 1,4-benzene radical which may be substituted,
E is the residue of a coupling component which is free from azo groups, at least one of A and M containing a phosphonic acid group, and the metal complexes of those having a metallisable group are reactive dyes suitable for use in the process of German OLS No. 2324809.

6 Claims, No Drawings

AZO DYESTUFFS

This invention relates to new azo dyestuffs containing one or more phosphonic acid groups.

According to the invention there are provided azo dyestuffs, which in the acid form, are represented by the formula:

A—N═N—M—N═N—E    (1)

wherein
A is an aromatic radical,
M is a 1,4-benzene radical which may be substituted,
E is the residue of a coupling component which is free from azo groups,
at least one of A and M containing a phosphonic acid group.

That is to say, the new dyestuffs may have a phosphonic acid group in A, in which case M need not contain a phosphonic acid group, or a phosphonic acid group in M, in which case A need not contain a phosphonic acid group, or a phosphonic acid group in both A and M.

A phosphonic acid group present in the radical M is preferably attached to the carbon atom of an alkylene, more especially a methylene group, present as a substituent on the benzene nucleus. In this case, M is a radical of the formula:

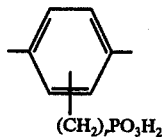
(2)

where
r is an integer, preferably 1.

As examples of radicals represented by M which are free from phosphonic acid groups, there may be mentioned, more especially, radicals of the formula:

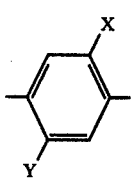
(3)

wherein
X is H, CH$_3$, lower alkoxy or carboxy, and
Y is H, CH$_3$, lower alkoxy, acylamino, e.g. acetylamino or ureido.

The terms "lower alkoxy" and "lower alkyl" used in this specification mean alkoxy or alkyl groups having 1 to 4 carbon atoms.

As examples of aromatic radicals represented by A which contain a phosphonic acid group there may be mentioned:

(a) Naphthalene or, preferably, benzene radicals which carry a phosphonic acid group attached to a carbon atom of the ring or of a substituent, e.g. an alkylene radical, attached to a carbon atom of the ring. The benzene or naphthalene radical can contain other substituents, e.g. fluorine, chlorine, bromine, lower alkyl, lower alkoxy, nitro, CO$_2$H, SO$_3$H;

(b) Radicals of the azobenzene, azonaphthalene or phenylazonaphthalene series in which one or both of the phenyl and naphthalene nuclei contain a phosphonic acid group attached as stated in (a) and which may be further substituted as stated in (a), e.g. radicals of the formula:

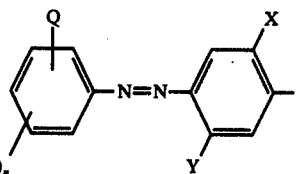
(4)

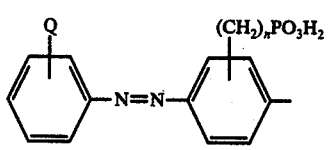
(5)

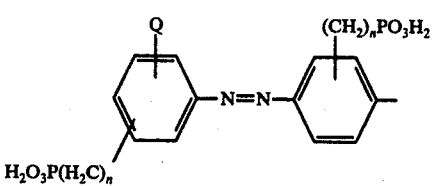
(6)

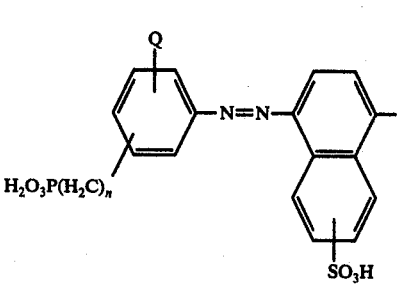
(7)

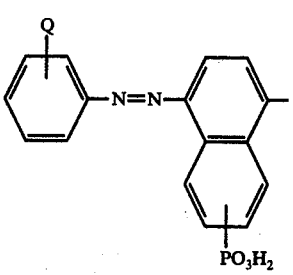
(8)

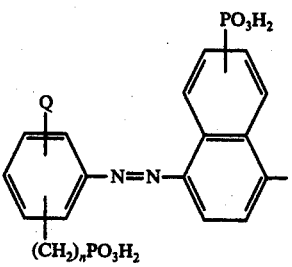
(9)

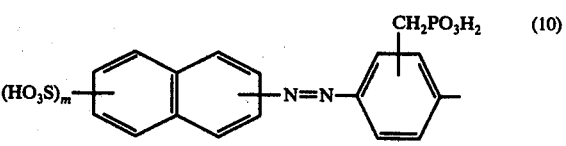
(10)

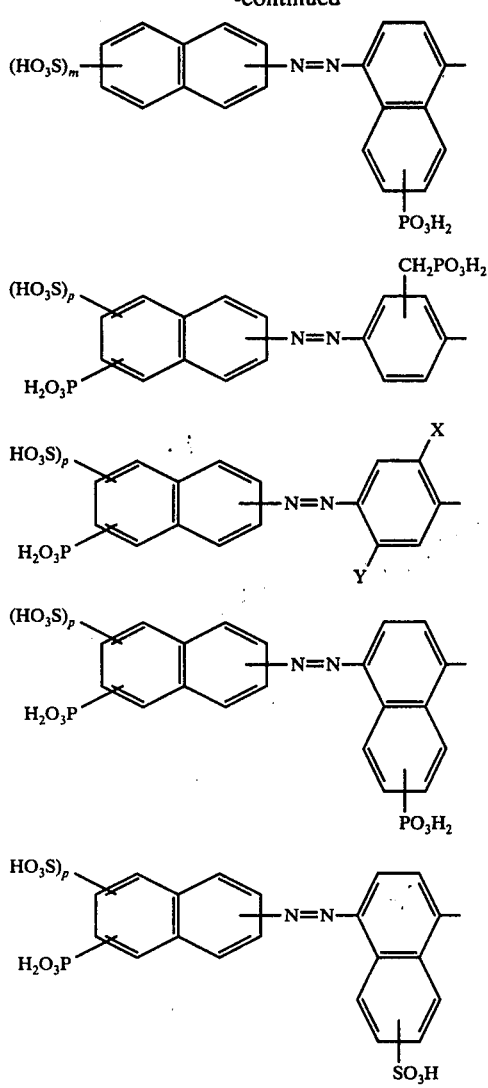

wherein
*n* is 0 or 1
*m* is 1, 2 or 3
*p* is 0, 1 or 2
Q is fluorine, chlorine, bromine, lower alkyl, lower alkoxy, nitro, carboxy or sulphonic acid, and
X and Y have the meanings stated above.

The preferred meaning of A is a benzene nucleus carrying a phosphonic acid group in meta position to the azo group.

As examples of aromatic radicals represented by A which are free from phosphonic acid groups, there may be mentioned:

Phenyl and α- or β-naphthyl, optionally substituted by fluorine, chlorine, bromine, lower alkyl, lower alkoxy, nitro, carboxy, aminosulphonyl, aminocarbonyl, $CF_3$, acylamino, e.g. acetyl-or benzoyl-amino, and/or $SO_3H$;

radicals containing two benzene nuclei, e.g. of the diphenyl, diphenyloxide, diphenylamine, diphenylethane, diphenyl sulphide, diphenyl sulphone, stilbene, benzanilide or benzene sulphonanilide series, which may be substituted by the substituents just mentioned above;

radicals of the azobenzene, azonaphthalene or phenylazonaphthalene series which may be substituted by the substituents mentioned above.

The symbol E in formula 1 can represent the residue of any coupling component which is free from azo groups, for example, coupling components of any of the following series:
naphthols
naphthol sulphonic acids
aminonaphthol sulphonic acids and N-substituted derivatives thereof, e.g. wherein the amino group is substituted by an alkyl or aryl radical, but more especially by an acyl, e.g. acetyl or benzoyl, radical or the residue of a halogeno heterocyclic compound such as cyanuric chloride or trichloropyrimidine,
p-coupling amines of the benzene and naphthalene series pyrazolones, hydroxy pyridones, barbituric acid, acetoacetarylides, aminopyrazoles and phenols.

The symbol E in formula (1) is intended to also include radicals resulting from further reactions on amino or hydroxyl groups in the residues of coupling component, e.g. methylation or acylation, which if carried out prior to coupling would convert the coupling component into a compound which does not itself couple.

According to a further feature of the invention there is provided a process for manufacture of the new azo dyestuffs which comprises coupling the diazonium salt from an aromatic amine of the formula:

$$A - N = N - M - NH_2 \quad (16)$$

wherein
A and M have the meanings stated above with a coupling component which is free from azo groups.

The above process can be carried out by methods common in the art for coupling diazotised aminoazo compounds with coupling components, e.g. by adding an aqueous solution or suspension of the diazonium salt to an aqueous suspension or solution of the coupling component, which is maintained at a suitable pH value, which, dependent on the coupling component, may be in the range of 2 to 9, and at a temperature from 0° C upwards.

As examples of coupling components which may be used in the above process, there may be mentioned:
1- and 2-naphthol
2-naphthol-6-sulphonic acid
1-naphthol-4- and 8-sulphonic acids
1-naphthol-4,8- , -3,6- and -3,8-disulphonic acids
2-naphthol-3,6- and -6,8-disulphonic acids
1-naphthol-3,6,8- and -4,6,8-trisulphonic acids
4,8-dichloro-1-naphthol
2-hydroxy-3-naphthoic acid and its arylamides, e.g. the anilide,
p-chloroanilide, p-methoxyanilide or 2,5-dimethoxyanilide
2-hydroxy-6-sulpho-3-naphthoic acid
1,8-aminonaphthol-4- and 5-sulphonic and 2,4-, 3,6- and 4,6-disulphonic acids
2,5-aminonaphthol-7-sulphonic and 1,7-disulphonic acids
2,8-aminonaphthol-6-sulphonic and 3,6- and 4,8-disulphonic acids
1,6-aminonaphthol-3-sulphonic acid
1,5-aminonaphthol-7-sulphonic acid
2,6-aminonaphthol-8-sulphonic acid
2-methylamino-8-naphthol-6-sulphonic acid
2-methylamino-5-naphthol-7-sulphonic acid the N-acetyl, N-benzoyl, N-sulphobenzoyl, m- and p-nitrobenzoyl, chloro-s-triazine and chloropyrimidine derivatives of these aminonaphthol sulphonic acids
1-phenylamino-8-naphthol-3,6-disulphonic acid
2-phenylamino-5-naphthol-7-sulphonic acid
2-phenylamino-8-naphthol-6-sulphonic acid
2-(3- and 4-sulphophenyl)amino-5-naphthol-7-sulphonic acids
2-(3- and 4-sulphophenyl)amino-8-naphthol-6-sulphonic acids
aniline
o- and m-toluidines
o- and m-anisidines
anthranilic acid
cresidine
2,5-xylidene
2,5-dimethoxyaniline
m-aminoacetanilide
m-phenylene diamine
m-aminophenyl urea
m-aminobenzyl phosphonic acid
1-naphthylamine
1-naphthylamine-6-, -7- and -8-sulphonic acids
1-naphthylamine-6,8-disulphonic acid
3-carboxy-5-pyrazolone
1-phenyl-3-methyl-5-pyrazolone
1-(2, 3 and 4-sulphophenyl)-3-methyl-5-pyrazolones
1-(2,5-dichloro-4-sulphophenyl)-3-methyl-5-pyrazolone
1-(2-methyl-3-amino-5-sulphophenyl)-3-methyl-5-pyrazolone
1-(4-amino-3-sulphophenyl)-3-methyl-5-pyrazolone
1-(3-amino-4-sulphophenyl)-3-methyl-5-pyrazolone
1-(4-nitro-3-sulphophenyl)-3-methyl-5-pyrazolone
1-(3-nitro-4-sulphophenyl)-3-methyl-5-pyrazolone
4-(3-methyl-5-pyrazolon-1-yl)-4'-nitrostilbene-2,2'-disulphonic acid
1-(4,8-disulphonaphth-2-yl)-3-methyl-5-pyrazolone
1-(6,8-disulphonaphth-2-yl)-3-methyl-5-pyrazolone
1-(4-sulphonamidophenyl)-3-methyl-5-pyrazolone
1-(3-carboxy-4-hydroxyphenyl)-3-methyl-5-pyrazolone
1-(2-methyl-5-chloro-4-sulphophenyl)-3-methyl-5-pyrazolone
1-(2-methyl-4,5-disulphophenyl)-3-methyl-5-pyrazolone
1-(2,5-disulphophenyl)-3-methyl-5-pyrazolone
1-(3-aminophenyl)-3-methyl-5-pyrazolone
the corresponding pyrazolones having a carboxylic acid group in place of the methyl group at the 3-position of the pyrazolone ring,
barbituric acid
1-phenyl-3-methyl-5-aminopyrazole
1-(3-sulphophenyl)-3-methyl-5-aminopyrazole
acetoacetanilide
acetoacet-2-chloroanilide
acetoacet-4-chloro-2,5-dimethoxyanilide
acetoacet-2- and 4-methoxyanilides
acetoacet-4-sulphoanilide
phenol
o-, m- and p-cresol
2,5-dimethylphenol
2, 3 and 4-methoxyphenol
2-carboxyphenol
2-carboxy-6-methylphenol
phenol-4-sulphonic acid
resorcinol
m-aminophenol
4-phenyl-2,6-dihydroxypyridine
1-ethyl-4-phenyl-6-hydroxypyrid-2-one
3-cyano-4-phenyl-2,6-dihydroxypyridine
4-methyl-2,6-dihydroxypyridine
3-cyano-4-methyl-2,6-dihydroxypyridine
3-aminocarbonyl-4-methyl-2,6-dihydroxypyridine
3,4-dimethyl-2,6-dihydroxypyridine
1,4-dimethyl-6-hydroxypyrid-2-one
1,3,4-trimethyl-6-hydroxypyrid-2-one
1,4-dimethyl-3-cyano-6-hydroxypyrid-2-one
1,4-dimethyl-3-aminocarbonyl-6-hydroxypyrid-2-one
1-ethyl-4-methyl-6-hydroxypyrid-2-one
1-ethyl-3-cyano-4-methyl-6-hydroxypyrid-2-one
1-ethyl-3-aminocarbonyl-4-methyl-6-hydroxypyrid-2-one
1-ethyl-3,4-dimethyl-6-hydroxypyrid-2-one
1-ethyl-3-chloro-4-methyl-6-hydroxypyrid-2-one
1-ethyl-3,4-trimethylene-6-hydroxypyrid-2-one and
1-n-butyl-3-sulpho-4-methyl-6-hydroxypyrid-2-one.

The aminoazo compounds of formula (16) can themselves be obtained by coupling a p-coupling amine of the benzene series with the diazonium salt of an aromatic amine, either or both of the two amines containing a phosphonic acid group.

As examples of p-coupling amines which may be used, there may be mentioned:
aniline
o- and m-toluidines
o- and m-anisidines
anthranilic acid
cresidine
2,5-xylidine
2,5-dimethoxyaniline
m-aminoacetanilide
m-aminophenylurea
m-aminobenzyl phosphonic acid.

The diazonium salt used should be derived from an aromatic amine which contains a phosphonic acid group if the p-coupling amine does not, but can be free from phosphonic acid groups if the p-coupling amine contains such a group. In the latter case it is usually preferable for the aromatic amine to contain a sulphonic or carboxylic acid group.

As examples of aromatic amines whose derived diazonium salts may be used, there may be mentioned:
(a) Aromatic amines containing a phosphonic acid group
o-, m- and p-aminophenyl phosphonic acids
3- and 4-aminobenzyl phosphonic acids
3-amino-4-methyl phenyl phosphonic acid
4-amino-2-fluorophenyl phosphonic acid
2-amino-5-chlorophenyl phosphonic acid
3-amino-4-chlorophenyl phosphonic acid
4-amino-2-bromophenyl phosphonic acid
4-amino-3-nitrophenyl phosphonic acid
1-naphthylamine-6- and -7-phosphonic acids
2-naphthylamine-7-phosphonic acid
5-sulpho-2-naphthylamine-7-phosphonic acid
8-sulpho-1-naphthylamine-3-phosphonic acid
4,8-disulpho-1-naphthylamine-3-phosphonic acid
also the monoazo compounds obtained by coupling the diazonium salts obtained from these amines with aromatic primary amines capable of coupling e.g.
aniline
m-toluidine
o-toluidine
2,5-dimethylaniline
o-anisidine
m-anisidine
2,5-dimethoxyaniline 5-methyl-2-methoxyaniline
anthranilic acid
4-methyl-2-aminobenzoic acid
3-acetylaminoaniline
m-ureidoaniline
3-acetylamino-6-methylaniline
3-acetylamino-6-methoxyaniline
3-benzoylaminoaniline
3-aminobenzylphosphonic acid
1-naphthylamine-6-sulphonic acid
1-naphthylamine-7-sulphonic acid
2-ethoxy-1-naphthylamine-6-sulphonic acid
1-naphthylamine-6-phosphonic acid
1-naphthylamine-7-phosphonic acid
also the monoazo compounds obtained by coupling an aromatic amine
which contains a phosphonic acid group and is capable of coupling, e.g. 3-aminobenzyl phosphonic acid
1-naphthylamine-6-phosphonic acid or
1-naphthylamine-7-phosphonic acid
which an aromatic diazonium salt, e.g. any of those mentioned in the above, or the following lists:

(b) Aromatic amines containing a sulphonic or carboxylic acid group
aniline-2,3 and 4-sulphonic acid
aniline-2,5-disulphonic acid
aniline-3,5-disulphonic acid
aniline-2,4-disulphonic acid
4- and 5-sulphoanthranilic acid
2-nitroaniline-4-sulphonic acid
4-nitroaniline-2-sulphonic acid
3-nitroaniline-6-sulphonic acid
5-nitro-2-aminoanisole-4-sulphonic acid
2-methylaniline-4,5-disulphonic acid
2,5-dichloroaniline-4-sulphonic acid
4-methylaniline-2-sulphonic acid
5-chloro-4-methylaniline-2-sulphonic acid
4-methoxyaniline-2-sulphonic acid
4-chloroaniline-3-sulphonic acid
5-acetylaminoaniline-2,4-disulphonic acid
anthranilic acid
2-aminoterephthalic acid
m-aminobenzoic acid
3- or 4-aminophthalic acid
p-aminobenzoic acid
5-nitroanthranilic acid
6-nitro-3-aminobenzoic acid
5-nitro-2-aminoterephthalic acid
1-naphthylamine-4-sulphonic acid
2-naphthylamine-4,8-disulphonic acid
6-nitro-2-naphthylamine-4,8-disulphonic acid
2-naphthylamine-6,8-disulphonic acid
2-naphthylamine-5,7-disulphonic acid
3- and 4-acetylaminoaniline-6-sulphonic acid
3-dichloro-s-triazinylaminoaniline-6-sulphonic acid
3-chloromethoxy-s-triazinylaminoaniline-6-sulphonic acid
2-aminoanisole-4- or 5-sulphonic acid
5-amino-2-hydroxybenzoic acid
1-naphthylamine-5, 6 or 7-sulphonic acid
2-naphthylamine-1, 5, 6, 7 or 8-sulphonic acid
1-naphthylamine-3,6-disulphonic acid
2-naphthylamine-1,5-disulphonic acid
2-naphthylamine-1,6-disulphonic acid
2-naphthylamine-6,8-disulphonic acid
6-acetylamino-2-naphthylamine-4,8-disulphonic acid
2-naphthylamine-3,6,8-trisulphonic acid
2-naphthylamine-4,6,8-trisulphonic acid (c) Aromatic amines free from sulphonic, carboxylic or phosphonic acid groups
aniline
o-, m- and p-toluidine
2,4- and 2,5-dimethylaniline
o-, m- and p-anisidine
2,4- and 2,5-dimethoxyaniline
5-methyl-2-methoxyaniline
o-, m- and p-chloroaniline
o-, m- and p-bromoaniline
2,4- and 2,5-dichloroaniline
4-chloro-2-trifluoromethylaniline
o-, m- and p-nitroaniline
2-chloro-4-nitroaniline
4-chloro-2-nitroaniline
4-chloro-3-nitroaniline
4- and 5-nitro-2-methoxyaniline
4- and 5-nitro-2-methylaniline
3-nitro-4-methoxyaniline
2-nitro-4-methylaniline
3- and 4-aminoacetanilide 4-amino-N-methylacetanilide
3-ureidoaniline
3- and 4-benzoylaminoaniline
3- and 4-benzenesulphonylaminoaniline
3-acetylamino-6-methylaniline
3-acetylamino-6-methoxyaniline
3- and 4-dichloro-s-triazinylaminoaniline
3- and 4-(trichloropyrimidinylamino)aniline
3- and 4-(cyanodichloropyrimidinylamino)aniline
3- and 4-(chlorodifluoropyrimidinylamino)aniline.

In some cases, it may be desirable to use the sulphamic acid derivative of the amine as the substance which is diazotised.

The new azo dyestuffs which contain a metallisable system can be converted to their heavy metal complexes, e.g. the 1:1-copper, nickel or cobalt complexes or the 1:2-chromium or cobalt complexes, by treatment with metal-yielding agents. These dyes form a further feature of the invention.

As examples of such dyes, there may be mentioned:
(a) the metal complexes of dyes of the formula

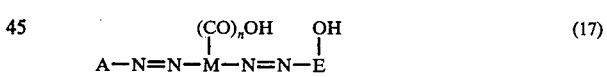

where $n$ is 0 or 1 and the $(CO)_nOH$ and OH groups in M and E, respectively, are ortho to the azo group linking M and E. In the case of copper complexes, these may also be obtained by the demethylative coppering of dyes of the formula

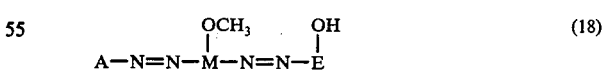

where the methoxy and hydroxyl groups are ortho to the azo group linking M and E; or by the oxidative coppering of dyes of the formula:

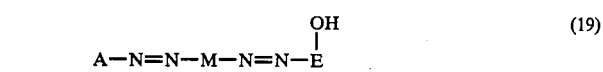

wherein the positions in M ortho to the azo group linking it to E are unsubstituted.
(b) dyes of the formula

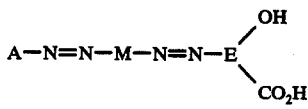
(20)

where the OH and CO₂H in E are in ortho position to each other.

The new azo dyestuffs which contain a phenolic hydroxyl group in E can be alkylated by treatment with an alkylating agent to convert the hydroxyl group to an alkoxy, more especially a methoxy or ethoxy group. As examples of such dyes, there may be mentioned:

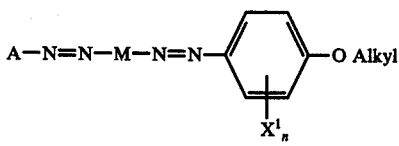
(21)

wherein $n$ is 0 or 1 and $X^1$ is methyl or methoxy. Alternatively they may be reacted with p-toluenesulphonyl chloride to form the p-toluenesulphonyloxy derivatives.

The new azo dyestuffs and also the derived copper complexes which contain an acylatable amino group in E can be acylated by reaction, e.g. with acid halides or anhydrides, or reacted with halogenated heterocyclic compounds, e.g. with acetic anhydride, acetyl chloride, chloroacetyl chloride, propionyl chloride, benzoyl chloride, cyanuric chloride, 2,4-dichloro-6-methoxy-s-triazine, 2,4-dichloro-6-(3-sulphophenylamino)-s-triazine, trichloropyrimidine, tetrachloropyrimidine, 5-cyanotrichloropyrimidine, 5-chlorotrifluoropyrimidine, 2,3-dichloroquinoxaline-6-carbonyl chloride, benzene sulphonyl chloride, p-toluenesulphonyl chloride or 2,3-dichloroquinoxaline-6-sulphonyl chloride.

The resultant dyes can be represented by the formulae:

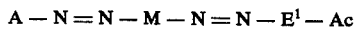
(22)

and

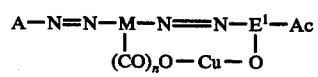
(23)

wherein $n$, A and M have the meanings stated above, $E^1$ is the residue of a coupling component containing an acylatable amino group and which in the case of formula (23) also contains a hydroxyl group ortho to the coupling position, and Ac is an acyl radical or the residue of a halogeno heterocyclic compound. Where Ac itself still contains unreacted halogen atoms these can be replaced, by customary methods, by hydrolysis or by reaction with ammonia or amines.

As preferred examples of such dyes, there may be mentioned more especially dyes of the formulae:

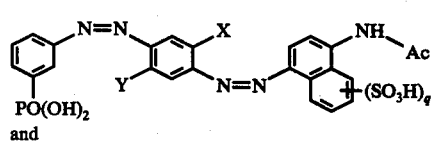
(24)

and

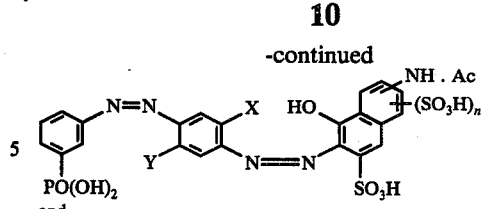
(25)

and

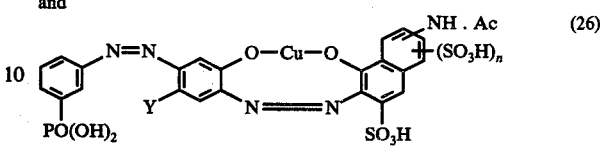
(26)

wherein $q$ is 1 or 2 and the symbols $n$, X, Y and Ac have the meanings stated above, and more especially dyes of the above formulae wherein Ac represents acetyl, benzoyl, a chloro-s-triazinyl radical of the formula:

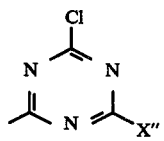
(27)

wherein $X''$ is Cl, OH, NH₂, OCH₃, a mono- or di-sulphonated anilino radical or a sulphonated toluidino, anisidino, chloroanilino or carboxyanilino radical, or a halogenopyrimidyl radical of the formula

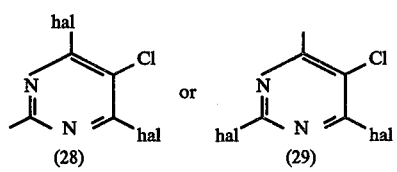

(28)    (29)

wherein hal is F or Cl, or of the formula:

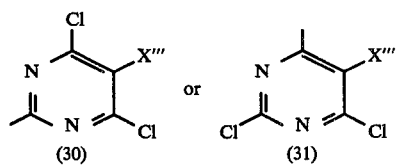

(30)    (31)

wherein $X'''$ is H, Cl or CN.

The new dyes can be isolated from the reaction mixture in which they have been prepared as solid products by conventional means such as spray-drying or by precipitation and filtration. They are preferably isolated in the acid form or in the form of the ammonium salt, or partly in one of these forms and partly as an alkali metal, e.g. Li, Na or K, salt. These salts can be obtained by adding a halide, e.g. the chloride, of the desired alkali metal, or an ammonium halide or ammonia to the completed reaction mixture before isolation. Alternatively, by addition of an alkanolamine, e.g. diethanolamine, to the completed reaction mixture, a highly soluble form of the dyestuff is obtained which can be used directly as a total liquor, for preparation of dye liquors or printing pastes.

The new dyestuffs are soluble in water owing to the presence of phosphonic acid groups. In many cases, there may also be sulphonic acid groups present to increase their solubility. They can be used, in general, for the colouration of textile materials which can be dyed by dyes solubilised by anionic groups, e.g. natural and synthetic polyamide materials, e.g. wool, silk, polyhexamethylene adipamide and polycaproimide, but more especially natural or regenerated cellulose textile materials, e.g. cotton, linen and viscose rayon; in the case of cellulose textile materials, they are preferably fixed on the fibre by application from an aqueous acidic solution and baking at a temperature of from 95° to 230° C in the presence of a carbodiimide e.g. cyanamide, dicyandiamide, e.g. by the method described in DOLS No. 2324809.

The new dyestuffs are particularly suitable for application to mixed fabrics of cellulose and synthetics, e.g. polyester materials, together with disperse dyes from a single dyebath or printing paste. In this respect, the new dyestuffs show an advantage over most conventional reactive dyes which are normally applied in the presence of alkaline fixing agents. The latter lead to flocculation of the majority of disperse dyes, so that the range of the latter which can be applied together with conventional reactive dyes in single dyebaths or printing pastes is very limited. In contrast, the acid fixing conditions used for the new dyes have no effect on disperse dyes and the two classes of dyes can be used together without difficulty.

The invention is illustrated by the following Examples in which parts are by weight.

EXAMPLE 1

A solution of 17.3 parts of 3-aminobenzene phosphonic acid in 200 parts of water is adjusted to pH 7 by the addition of a concentrated solution of ammonia. 7 parts of sodium nitrite are added and the solution is cooled below 5° C and then run into a mixture of 100 parts of ice and 20 parts of concentrated hydrochloric acid. The solution is stirred for 30 minutes and the slight excess of nitrous acid is removed by addition of sulphamic acid. The diazonium compound so obtained is added to a stirred solution of 13.7 parts of 2-methoxy-5-methylaniline in 500 parts of water and 12 mparts of concentrated hydrochloric acid. Ammonium acetate is added to bring pH of the mixture to 5 and the mixture is stirred at below 10° C for 16 hours. Ammonium chloride (10% w/v) is added and the mixture is filtered. 3.69 parts of the aminomonoazo compound so obtained are dissolved in 80 parts of water, 0.7 part of sodium nitrite is added and the resultant solution is poured into a stirred mixture of 50 parts of ice, 20 parts of water and 5 parts of concentrated hydrochloric acid. The mixture is stirred at 0°–10° C for 1 hour, then the excess nitrous acid is removed by the addition of sulphamic acid. A solution of 3.3 parts of 2-amino-5-naphthol-1,7-disulphonic acid in 50 parts of water is adjusted to pH 7 by the addition of a concentrated solution of ammonia and the above diazonium salt is added. The reaction mixture is stirred at below 5° C for 1 hour, the pH being maintained at 7 to 8 by the addition of a concentrated aqueous solution of ammonia. Ammonium chloride 15% w/v is added and the precipitated disazo compound is filtered off and is then dried.

The dyestuff, so obtained, when applied to cellulosic textile materials by the methods disclosed in OLS No. 2324809 yields violet dyeings with excellent fastness to wet treatments.

The following Table gives further examples of dyestuffs of the invention which may be obtained by the procedure of Example 1 but using the equivalent amount of the compound listed in column 2 in place of the 3.3 parts of 2-amino-5-naphthol-1,7-disulphonic acid used in Example 1. The shade of the dye is given in column 3.

| Ex. | Compound | Shade |
|---|---|---|
| 2 | 2-acetylamino-8-naphthol-6-sulphonic acid | dull violet |
| 3 | 1,8-aminonaphthol-3,6-disulphonic acid | blue |
| 4 | 1-(5-cyano-2,4-dichloropyrimidyl)amino-8-naphthol-3,6-disulphonic acid | blue |
| 5 | 2-naphthol-3,6-disulphonic acid | violet |
| 6 | 1-(4-sulphophenyl)-3-carboxy-5-pyrazolone | red |
| 7 | m-aminophenol | dull violet |
| 8 | acetoacet-2-chloroanilide | yellow |

Table 2 gives further examples of new dyestuffs of the invention which are obtained in a similar manner to the method described in Example 1 by coupling 1 molecular proportion of the diazonium salt of the amine A listed in column 2 with the p-coupling amine M listed in column 3 and diazotising and coupling the aminoazo compound so obtained with one molecular proportion of the coupling component E listed in column 4. The shade of the dye obtained is listed in column 5 of the table.

TABLE 2

| Example | A | M | E | shade |
|---|---|---|---|---|
| 9 | 3-aminophenyl phosphonic acid | 2-methoxy-5-methylaniline | 2-amino-8-naphthol-3,6-disulphonic acid | Grey |
| 10 | " | " | 1-naphthol-3,6-disulphonic acid | Violet |
| 11 | " | " | 2-naphthol-6-sulphonic acid | " |
| 12 | " | " | 1-amino-8-naphthol-4,6-disulphonic acid | Blue |
| 13 | " | " | 1-benzoylamino-8-naphthol-3,6-disulphonic acid | " |
| 14 | " | " | 1-N-acetylamino-8-naphthol-4,6-disulphonic acid | " |
| 15 | " | " | 1-amino-8-naphthol-5,7-disulphonic acid | " |
| 16 | " | " | 2(N-acetyl-N-methylamino)-8-naphthol-6-sulphonic acid | Violet |
| 17 | " | " | 1-(2',5'-dichloro-4'-sulphophenyl)-3-methyl-5-pyrazolone | Red |
| 18 | " | aniline | 2-amino-5-naphthol-1,7-disulphonic acid | " |
| 19 | " | o-toluidine | 1-amino-8-naphthol-3,6-disulphonic acid | Violet |
| 20 | " | m-anisidine | " | " |
| 21 | 1-Naphthylamine-2,5,7-trisulphonic acid | 3-aminobenzyl phosphonic acid | 2-naphthol | " |
| 22 | " | " | 1-amino-8-naphthol-3,6-disulphonic acid | " |
| 23 | " | " | 1-N-acetylamino-8-naphthol-3,6-disulphonic acid | " |
| 24 | " | " | 1-naphthol-3,6-disulphonic acid | " |
| 25 | " | " | salicylic acid | Dull yellow |
| 26 | " | " | 1,3-phenylenediamine | Brown |
| 27 | " | " | 1-naphthylamine-6-sulphonic acid | Violet |
| 28 | 4-aminophenylphosphonic acid | " | 1-N-acetylamino-8-naphthol-3,6-disulphonic acid | " |

TABLE 2-continued

| Example | A | M | E | shade |
|---|---|---|---|---|
| 29 | " | aniline | 2-amino-5-naphthol-1,7-disulphonic acid | Red |
| 30 | 3-aminophenyl phosphonic acid | 3-aminoacetanilide | 1-N-acetylamino-8-naphthol-4,6-disulphonic acid | Violet |
| 31 | " | 3-aminobenzyl phosphonic acid | 1,3-phenylenediamine | Brown |
| 32 | " | 2-methoxy-5-methylaniline | 1-(4'-sulphophenyl)-3-methyl-5-pyrazolone | Red |
| 33 | " | " | 1-ethyl-3-aminocarbonyl-4-methyl-6-hydroxypyrid-2-one | " |
| 34 | " | anthranilic acid | 1-naphthylamine-7-sulphonic acid | Violet |
| 35 | " | m-toluidine | 1-naphthol-3,6-disulphonic acid | " |
| 36 | " | o-toluidine | 1-naphthol-4-sulphonic acid | " |
| 37 | 4-aminophenyl phosphonic acid | aniline | 1-amino-8-naphthol-5,7-disulphonic acid | " |
| 38 | 3-aminophenyl phosphonic acid | 2,5-dimethoxyaniline | 1-amino-8-naphthol-3,6-disulphonic acid | Blue |
| 39 | " | " | 1-N-acetylamino-8-naphthol-3,6-disulphonic acid | " |
| 40 | " | m-toluidine | " | Violet |
| 41 | " | 2-methoxyaniline | " | Blue |
| 42 | " | 2,5-dimethoxyaniline | 1-amino-8-naphthol-5,7-disulphonic acid | Blue |
| 43 | 2-sulphoaniline | 3-aminobenzylphosphonic acid | 1-N-acetylamino-8-naphthol-3,6-disulphonic acid | Violet |
| 44 | 2-aminophenyl phosphonic acid | cresidine | 1-naphthol-3,6,8-trisulphonic acid | " |
| 45 | 1-naphthylamine-6-phosphonic acid | " | " | " |
| 46 | 1-naphthylamine-7-phosphonic acid | 3-aminobenzyl phosphonic acid | " | " |
| 47 | 3-amino-4-chlorophenyl phosphonic acid | 2,5-dimethoxyaniline | " | " |
| 48 | 3-amino-4-methoxyphenyl phosphonic acid | " | 2,4-diaminobenzene sulphonic acid | Brown |
| 49 | 4-amino-3-nitrophenyl phosphonic acid | aniline | 1-naphthol-3,6,8-trisulphonic acid | Violet |
| 50 | 3-amino-4-methylphenyl phosphonic acid | o-anisidine | 1-naphthol-4,6,8-trisulphonic acid | " |
| 51 | 2-aminonaphthalene-7-phosphonic acid | aniline | " | " |
| 52 | 3-aminophenyl phosphonic acid | 2,5-dimethylaniline | 1-N-acetylamino-8-naphthol-3,6-disulphonic acid | " |
| 53 | 4-aminophenylphosphonic acid | " | 1-naphthol-3,6,8-trisulphonic acid | " |
| 54 | 2-(4'-amino-2'-phosphono-methylphenylazo)-naphthalene 4,8-disulphonic acid | 2-methoxy-5-methylaniline | 1-amino-8-naphthol-3,6-disulphonic acid | Blue |
| 55 | 4-(3'-phosphonophenylazo)-1-aminonaphthalene-6-sulphonic acid | 2-methoxyaniline | 2-amino-5-naphthol-1,7-disulphonic acid | " |
| 56 | 1-amino-3-phosphonomethyl-4(2',5'-disulphophenylazo)-benzene | 2,5-dimethoxyaniline | 2-amino-5-naphthol-7-sulphonic acid | " |
| 57 | 3-aminophenyl phosphonic acid | aniline | 2-naphthol-6,8-disulphonic acid | Scarlet |
| 58 | " | " | 1-naphthol-3,6-disulphonic acid | Violet |
| 59 | " | 2-methoxy-5-methylaniline | 1-N-phenylamino-8-naphthol-3,6-disulphonic acid | Blue |
| 60 | " | " | 1-ethyl-4-methyl-3-sulphomethyl-6-hydroxypyrid-2-one | Red |
| 61 | " | " | 1-naphthol-4-sulphonic acid | Violet |
| 62 | " | anthranilic acid | 1-amino-8-naphthol-3,6-disulphonic acid | " |
| 63 | " | 2-methoxy-5-methylaniline | 1-(N-2',4'-dichloro-s-triazinyl-6-yl-amino)-8-naphthol-3,6-disulphonic acid | Blue |
| 64 | " | " | 1-(N-2'-chloro-4'-amino-s-triazinyl-6-ylamino)-8-naphthol-3,6-disulphonic acid | " |
| 65 | " | " | 2-[N-2'-chloro-4'-(4"-sulpho-2"-carboxyanilino)-s-triazin-6'-ylamino]-8-naphthol-6-sulphonic acid | Blue-grey |
| 66 | " | " | 1-naphthylamine-6-sulphonic acid | Violet |
| 67 | " | m-toluidine | " | " |
| 68 | " | anthranilic acid | 1-naphthylamine-8-sulphonic acid | " |
| 69 | " | " | m-aminophenyl urea | Brown |
| 70 | " | aniline | 1-naphthylamine-8-sulphonic acid | Violet |
| 71 | " | o-anisidine | 1-amino-8-naphthol-4,6-disulphonic acid | Blue |

EXAMPLE 72

A mixture of 21.5 parts of the ammonium salt of 2-amino-6-[2'-methoxy-5'-methyl-4'-(3"-phosphonophenylazo)phenylazo]-5-naphthol-1,7-disulphonic acid prepared as in Example 1, 200 parts of water, 40 parts of a 2N aqueous solution of copper sulphate and 20 parts of a concentrated aqueous solution of ammonia is stirred at a temperature between 95° and 100° C for 15 hours. 45 parts of ammonium chloride are added and the precipitated metal complex is filtered off and dried.

The dyestuff composition so obtained when applied to cellulose textile materials by the methods described in OLS No. 2324809 yields blue shades having good fastness to light and to wet treatments.

Those of the dyes of Table 2 which are obtained from a middle component M containing a carboxylic acid or methoxy group ortho to the amino group and a coupling component E which contains a hydroxyl group ortho to the coupling position, can be converted to copper complexes in a similar manner to Example 72. Thus, starting from the dyestuffs given in column 2 of Table 3 below, copper-complex dyestuffs are obtained having the shade started in the third column.

Table 3

| Example | Dyestuff of Example: | Shade |
|---|---|---|
| 73 | 10 | Violet |
| 74 | 13 | Blue |
| 75 | 15 | " |
| 76 | 17 | Rubine |
| 77 | 32 | " |
| 78 | 38 | Blue |
| 79 | 41 | " |
| 80 | 55 | " |
| 81 | 62 | Violet |

EXAMPLE 82

A solution of 10.7 parts of the trisodium salt of the dyestuff of Example 3 in 100 parts of water is added to a stirred suspension of 2.9 parts of cyanuric chloride in 15 parts of acetone, 10 parts of ice and 20 parts of water. The mixture is stirred at 0°-10° C for 1 hour and is then neutralised carefully to pH 6 by addition of an aqueous solution of ammonia. When condensation is complete, ammonium chloride 10% w/v is added and the precipitated compound is filtered off and is then dried. The dyestuff so obtained when applied to cellulosic textile materials by the methods disclosed in OLS No. 2,324,809 yields blue dyeings with excellent fastness to wet treatments.

EXAMPLE 83

3-Aminobenzene phosphonic acid is diazotised and coupled in acid medium with an equimolar proportion of 3-aminobenzylphosphonic acid. The aminoazo compound so obtained is diazotised and coupled in acid medium with an equimolar proportion of m-aminophenyl urea. A solution of 12.5 parts of the tetrasodium salt of the aminodisazo compound so obtained, in 200 parts of water is added to a solution of 6.9 parts of the monosodium salt of 3-(N-2',4'-dichloro-s-triazin-6'-ylamino)-benzene sulphonic acid in 50 parts of water and the reaction mixture is heated at 35°-50° C for 2 hours, the pH of the mixture being maintained at 6-6.5 by the addition of sodium carbonate. When condensation is complete, ammonium chloride 10% w/v is added and the precipitate is filtered off and is then dried.

The dyestuff so obtained when applied to cellulose textile materials by the methods of OLS No. 2,324,809 yields orange-brown shades having excellent fastness to wet treatments.

Table 4 gives further examples of dyestuffs obtained in a similar manner to Examples 82 and 83 by reacting the dyestuff of column 2 with the heterocyclic compound named in column 3. The shade is given in column 4.

TABLE 4

| Ex. | Dyes of Example | Heterocyclic compound | Shade |
|---|---|---|---|
| 84 | 67 | m-(2,4-dichloro-5-triazin-6-ylamino)-sulphonic acid | Brown |
| 85 | 66 | p-(2,4-dichloro-s-triazin-6-ylamino)-sulphonic acid | " |
| 86 | 34 | cyanuric chloride | " |
| 87 | 68 | " | " |
| 88 | 69 | N-(2,4-dichloro-s-triazin-6-yl)aniline-2,5-disulphonic acid | Orange-brown |
| 89 | 70 | cyanuric chloride | Brown |
| 90 | 71 | " | Blue |

EXAMPLE 91

To a solution of 8.65 parts of the dichlorotriazinyl aminodisazo dyestuff described in Example 82, a solution of 2.0 parts of the monoammonium salt of metanilic acid in 20 parts of water is added. The mixture is stirred at 35°-40° C for 20 minutes, then the pH of the mixture is adjusted to pH 6 by the addition of an aqueous solution of ammonia and stirring is continued for a further 1½ hours, the pH being maintained at 6 by further addition of aqueous ammonia if necessary. When condensation is complete, ammonium chloride 18% w/v is added and the precipitated compound is filtered off and is then dried.

The dyestuff so obtained, when applied to cellulose textile materials by the methods disclosed in OLS No. 2,324,809, yields shades similar to those of Example 82 and having excellent fastness to wet treatments.

EXAMPLE 92

In a similar manner to Example 91, 13.18 parts of the product of Example 89 are condensed with 2.74 parts of p-aminobenzoic acid. The product dyes cotton in brown shades.

EXAMPLE 93

In a similar manner to Example 91, 14.7 parts of the product of Example 90 are condensed with 3.754 parts of N-methylmetanilic acid. The product dyes cotton in blue shades.

EXAMPLE 94

To a solution of 8.7 parts of 4-amino-3-methoxy-5-methylazobenzene-3'-phosphonic acid (prepared as described in Example 1) in 120 parts of water, there is added 1.9 parts of sodium nitrite and the resultant solution is poured into a stirred mixture of 50 parts of ice, 60 parts of water and 7 parts of concentrated hydrochloric acid. The mixture is stirred at 0°-10° C for 1 hour, then the excess nitrous acid is removed by the addition of sulphamic acid. The diazonium salt so obtained is added to a solution of 3.0 parts of sodium phenate in 40 parts of water, the pH of the mixture being maintained at 8 by the addition of sodium carbonate. After stirring overnight sodium chloride 5% w/v is added and the precipitate is filtered off. The residue on the filter is redissolved in water by addition of aqueous sodium hydroxide solution at pH 9, and the solution set stirred at 30° C. 9 parts of dimethylsulphate are added, the pH being maintained at 9 by the addition of aqueous sodium hydroxide solution and the mixture is stirred for 6 hours when methylation is complete. The mixture is filtered, the residue on the filter is washed with 20 parts of water and is then dried.

The dyestuff so obtained when applied to cellulosic textile materials by the methods of OLS No. 2,324,809 yields yellow-brown shades having excellent fastness of wet treatments.

EXAMPLE 95

16 parts of 4-amino-3-methoxy-6-methyl-1,1'-azobenzene-3'-phosphonic acid are dissolved in 100 parts of water by the addition of diethanolamine and to the solution, there are added 3.5 parts of sodium nitrite. The resultant solution is added with stirring to a mixture of 50 cc of water, 6 parts of 36% hydrochloric acid and 25 parts of ice, the temperature of the mixture being maintained at 10° ± 5° C by external cooling. The mixture is stirred for ½ with excess nitrous acid present then the latter is removed by the addition of sulphamic acid. 18.3 parts of 1-acetylamino-8-naphthol-3,6-disulphonic acid are dissolved in 120 parts of water by the addition of diethanolamine. The above diazonium mixture is added to the solution of 1-acetylamino-8-naphthol-3,6-disulphonic acid, the pH being maintained at 7 by the addition of diethanolamine. Coupling is complete after 2 hours.

The solution so obtained can be used directly for making up dyebaths or printing pastes for the colouration of cellulose textile materials by the methods described in OLS No. 2,324,809 and yields blue shades having excellent fastness to wet treatments.

We claim:

1. An azo dyestuff having the formula

wherein

A is a benzene radical having a phosphonic acid group and optionally containing a further substituent selected from the group consisting of methyl, chlorine, methoxy and nitro, M is a 1,4 phenylene radical optionally containing up to 2 substituents selected from the group consisting of methyl, methoxy, phosphonomethyl, acetylamino and carboxylic acid, and E is the residue of a coupling component selected from the group consisting of naphthol sulphonic acid, aminonaphthol sulphonic acid and lower alkanoylaminonaphthol sulphonic acid.

2. Azo dyestuffs as claimed in claim 1 wherein A is a benzene nucleus carrying a phosphonic acid group in meta position to the azo group.

3. Azo dyestuffs as claimed in claim 1 which are in the form of the ammonium salt.

4. Azo dyestuffs as claimed in claim 1 which are partly in the form of the free acid or ammonium salt and partly in the form of an alkali metal salt.

5. Aqueous preparations containing an azo dyestuff as claimed in claim 1 in the form of an alkanolamine salt.

6. The azo dyestuff of claim 1 having the formula

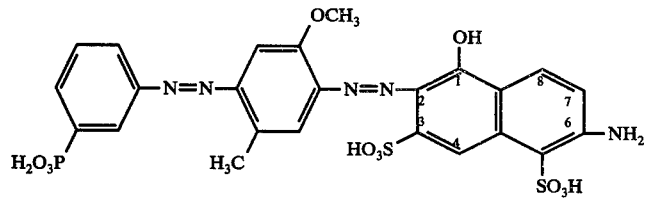

and being in the form of the ammonium salt.

* * * * *